United States Patent
Michniewicz

[11] Patent Number: 5,868,692
[45] Date of Patent: Feb. 9, 1999

[54] THERAPEUTIC DEVICE FOR WRIST INJURIES

[76] Inventor: Jan F. Michniewicz, 222 Holland Ave., San Antonio, Tex. 78212

[21] Appl. No.: 889,310

[22] Filed: Jul. 8, 1997

Related U.S. Application Data

[60] Provisional application No. 60/016,094 Jul. 8, 1996.

[51] Int. Cl.[6] .............................. A61F 3/00; A61F 13/00
[52] U.S. Cl. .................................. 602/21; 602/20; 602/64
[58] Field of Search ............................... 602/5, 6, 20–22, 602/62, 64; 128/878, 879; 2/16, 20

[56] References Cited

U.S. PATENT DOCUMENTS

| | | | |
|---|---|---|---|
| 1,313,344 | 8/1919 | Smart | 602/6 |
| 1,926,690 | 9/1933 | Stewart | 128/881 |
| 2,703,082 | 3/1955 | Emert | 128/881 |
| 3,938,509 | 2/1976 | Barber | 602/21 |
| 4,479,648 | 10/1984 | Alivo, Jr. | 602/21 X |
| 4,883,073 | 11/1989 | Aziz | 128/878 |
| 5,058,576 | 10/1991 | Grim et al. | 602/21 |
| 5,409,451 | 4/1995 | Daneman | 602/6 X |
| 5,713,836 | 2/1998 | O'Keefe | 602/5 |

OTHER PUBLICATIONS

San Antonio TX, Sep. 9, 1996, Thelma Garza, The growing menace of RSI, Newspaper article in S.A. life section of Sep. 9, 1996 section of the San Antonio Express–News (p. 1 and 10C).

Primary Examiner—Richard J. Apley
Assistant Examiner—Denise Pothier

[57] ABSTRACT

A wrist brace useful for therapeutic recovery and restraint of hand pronation and supination, with respect to the forearm, of approximately plus or minus 10°, while allowing relatively unrestricted lateral movement of said hand with respect to said forearm.

6 Claims, 5 Drawing Sheets

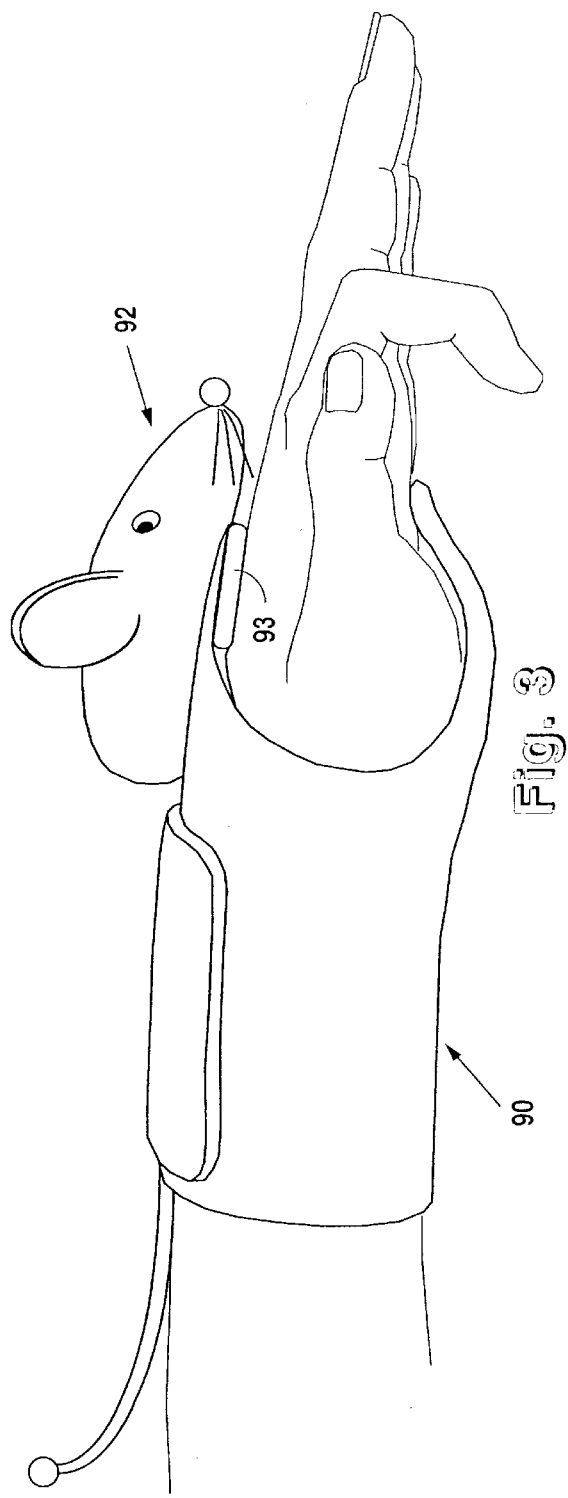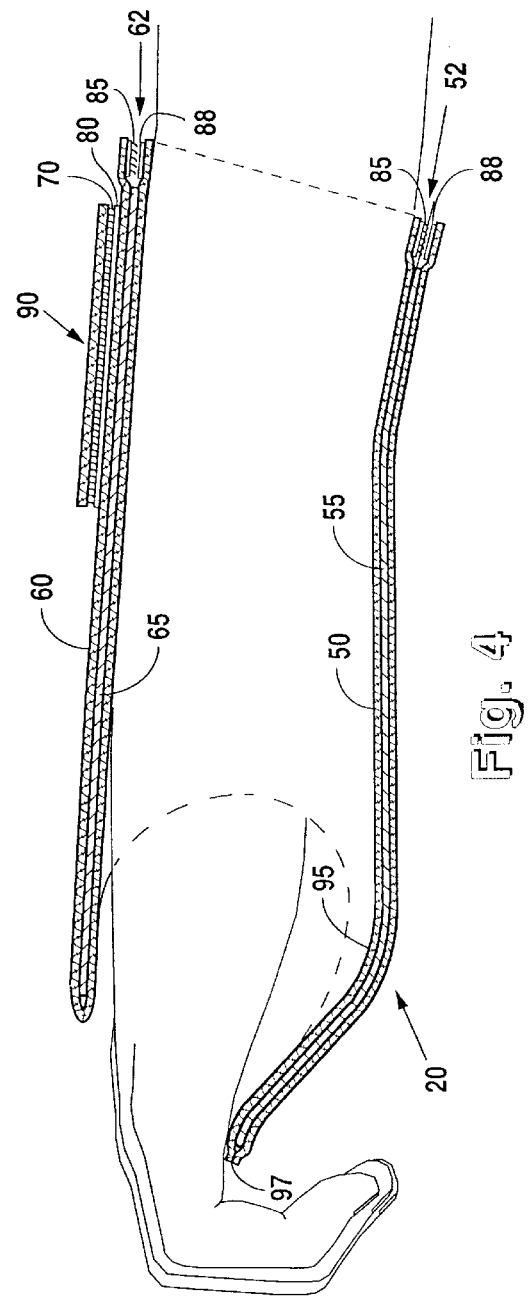

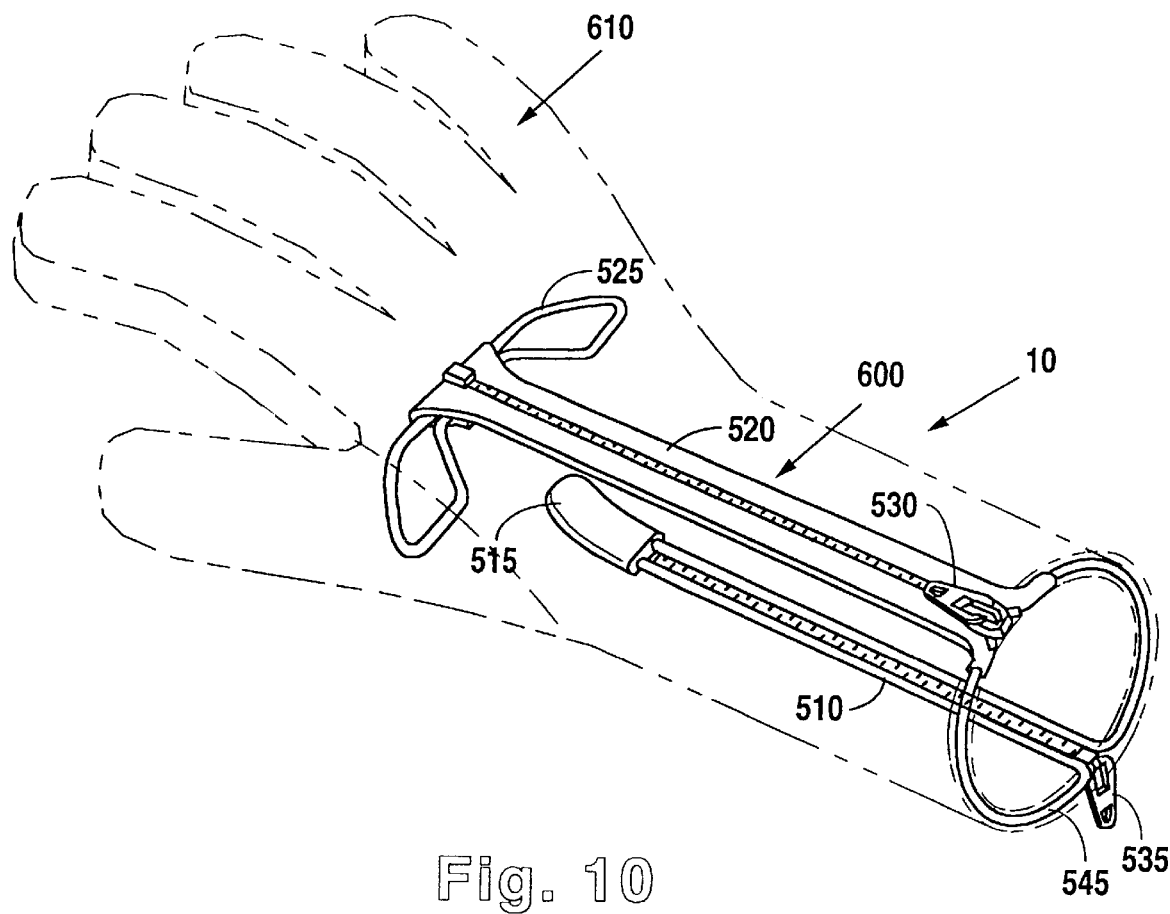

THERAPEUTIC DEVICE FOR WRIST INJURIES

BACKGROUND OF THE INVENTION

This application claims the benefit of the filing date of the provisional application number 60/016,094 which was filed on Jul. 8, 1996.

1. Field of The Invention

This invention relates generally to the field of restraining devices which assist in the therapeutic recovery from wrist injury brought about by trauma or strain. More particularly, the invention relates to an improved wrist restraint device which provides limited hand movement for the accomplishment of every day tasks, but restrains the wearer in such a way as to prevent extreme pronation or supination of the hand.

2. Background Information

The present invention is a distinct improvement over the prior art by virtue of its therapeutic effectiveness (restricts movement without the application of compressive force on the wrist), ease of use, combined with simplified construction which provides for ease of manufacture. Other advantages which accrue from the improved design include the ability to accomplish tasks which were not possible with the prior art, and the ability to use a single device for either the left or right hands.

The prior art was developed to assist those individuals who suffer from Cumulative Repetitive Stress Syndromes (CRSS) such as tendinitis, Carpal Tunnel Syndrome, and general tissue pain due to a lack of wrist support. The prior art has also been developed to assist individuals who, because of prior injury, suffer pain whenever they experience extreme pronation or supination of the hand. Excessive mechanical stress in the shoulders can also result from improper wrist support.

Heretofore, the prior art has tended to rigidly confine the wrist, compress the muscles of the forearm, and generally prevent pronation of the hand. However, such prior art devices are ineffective for several reasons. First, rigid confinement of the wrist makes it difficult to accomplish daily tasks. For example, typing or playing the piano, when done properly, utilize a relatively straight wrist posture. However, absolute rigidity is a hindrance and muscle weakening device, rather than a help. Small movements of the wrist are necessary to allow for normal muscular work and the extra amount of reach sometimes needed to access a particular key. Second, compression of the forearm muscles also acts to restrict movement. While such compression does act to support the wrist and confine movement, it may do so at the expense of smaller movements which do not cause pain, but are helpful in the accomplishment of tasks which require dexterity. Also, compression usually requires some type of covering which causes the forearm to sweat and accumulate bacteria and dirt. Such covering is inconvenient, psychologically and physically restrictive, and necessitates frequent removal of the covering to allow for cleaning of the skin so confined, as well as the covering itself. Finally, merely supporting the palm of the hand to prevent extreme pronation does nothing to prevent extreme supination. Some prior art devices overcome this problem by providing a small strap which is wrapped around the base of the thumb and an upper support, but the end result is that all of them use compressive force to restrict movement, and the same device cannot be used on both the left and right hand—the supination restraining strap must be located in one place on one device for the left hand, and located in another place for a right-handed device.

SUMMARY OF THE INVENTION

The present invention, in its preferred embodiment, comprises a Wire Brace (WeBe™, pronounced WeBe) made from a single piece of wire, such as that commonly used to make heavy coat hangers. The wire is formed in such a way that it loosely encircles the forearm of the wearer, extends along the lower and upper forearm past the wrist, with the lower support bending at approximately mid-palm to form a semi-circle and meet with the wire which has been similarly bent at approximately the middle of the back of the hand, at a point approximately ½ inch away from the junction formed by the thumb and index finger.

A typical embodiment of the invention would be formed in the manner described above, and would also be provided with a rubberized or foam cover material for user comfort.

The unique design of the device and particularly, the relatively ductile material from which it is formed, enables it to be worn on either the left or right hand, and easily modified to better fit the particular structure of the wearer's hand (e.g., large-boned vs. small-boned, etc.). Further, the unique construction of the device allows it to be made into (or worn under) a glove for use by athletes such as cyclists, swimmers, etc.

The unique structure of the device, when implemented in the form of the preferred embodiment, allows use during athletic contests, such as swimming, where moisture or sweat are to be frequently encountered. The unique construction of the device also allows it to be used unobtrusively in the office or meeting environment, with most of the device concealed beneath the wearer's sleeve. The device can be formed to imitate jewelry, and various accessories, such as a watch, pager, a pen holder, a toy for children, or other item can be attached to the portion of the device which extends over the back of the wearer's hand.

Finally, the wire brace contributes to strengthening of the wearer's muscles, rather than weakening them. That is, since the muscles of the forearm are not compressed, the wearer is free to move and exercise them, rather than allow them to atrophy due to disuse and immobilization.

Accordingly, an object of the present invention is to provide an improved wire brace of unitary construction.

A further object of the present invention is to provide an improved wire brace that is easy to manufacture.

Another object of the present invention is to provide an improved wire brace that is wearable on either the left or right hand.

Still another object of the present invention is to provide an improved wire brace that does not compress or immobilize the muscles of the forearm and wrist.

Yet another object of the present invention is to provide an improved wire brace constructed in such a manner as to allow air to freely circulate about the wearer's skin.

Yet another object of the present invention is to provide an improved wire brace which prevents extreme pronation or supination of the hand, while allowing a minimal amount of such movement for the accomplishment of everyday tasks.

A further object of the present invention is to provide an improved wire brace which presents an improved aesthetic appearance over the prior art.

Another object of the present invention is to provide an improved wire brace which can accommodate attached accessories, so as to be of increased utility over the prior art.

Still another object of the present invention is to provide an improved wire brace which can be easily modified or adapted by the wearer to accommodate various hand sizes.

Still another object of the present invention is to provide an improved wire brace which is more comfortable to wear than the prior art.

A further object of the present invention is to provide an improved wire brace which does not act to rigidly confine wrist movement.

Still another object of the present invention is to provide an improved wire brace which allows the wearer to strengthen his muscles through use, rather than allowing them to atrophy due to rigid confinement or compression.

Other objects and advantages of the present invention will become apparent in the following specifications when considered in light of the attached drawings, wherein a preferred embodiment of the invention is illustrated.

BRIEF DESCRIPTION OF THE DRAWINGS

FIG. 3 is a side view of a first alternative embodiment as applied to the wearer's hand.

FIG. 4 is a sectional side-view of a first alternative embodiment.

FIG. 10 is a perspective view of the third alternative embodiment, encased within a glove.

DETAILED DESCRIPTION OF THE PREFERRED EMBODIMENT

Figure 1:
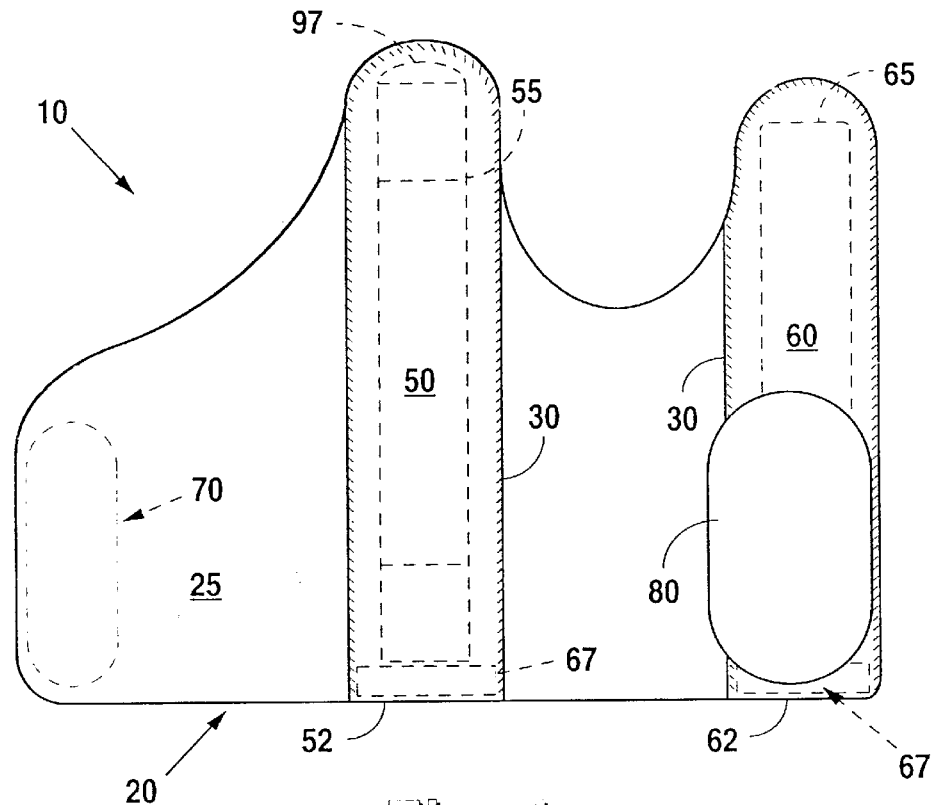
FIG. 1 is a top view of a first alternative embodiment.
Figure 2:
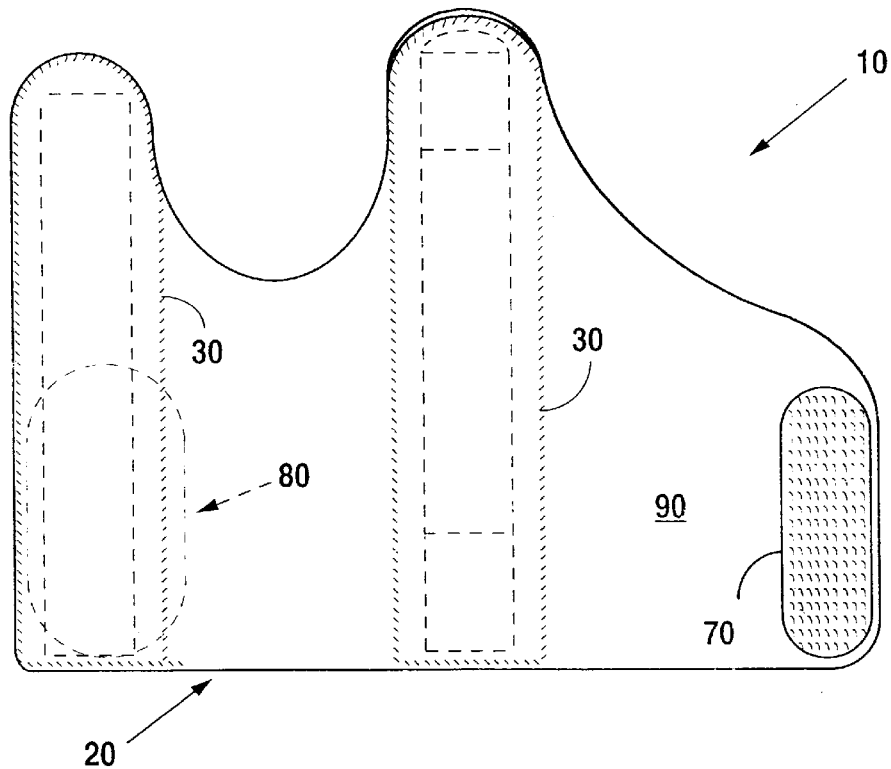
FIG. 2 is a bottom view of a first alternative embodiment.

Turning now to FIGS. 1, 2, 3, and 4, a top view of a first alternative embodiment of the present invention can be seen. This particular alternative embodiment is presented before the preferred embodiment illustration because, while it appears very similar to the prior art, it accomplishes most of the innovations provided by the instant invention. In this illustration, the Movement Restriction Cage (MRC™) 10 can be seen. Wrap 20 is cut to roughly the shape shown. Bonded to wrap inside 25, via stitching 30 in this case, is lower insert cover 50 and upper insert cover 60. Stitching 30 is used to form two pockets: the first between wrap inside 25 and lower insert cover 50, with lower insert opening 52, and the second between wrap inside 25 and upper insert cover 60 with upper insert opening 62. Each of the aforesaid pockets is formed to accept an insert, usually made of metal or plastic. In this case, lower insert 55 and upper insert 65 can be formed as rigid elements, or with some degree of springiness to accommodate the therapeutic needs of the wearer. To maintain the position of lower insert 55 and upper insert 65 in their respective locations during use, insert closures 67 are provided, and can be effected by use of Velcro® or snaps, etc. Cage closure loops 80, applied to wrap inside 25, are used to permit application of the Movement Restriction Cage 10 to the wearer's hand. Cage closure hooks 70 have been applied to part of the surface of wrap outside 90. Such application can be easily viewed in FIG. 3. To properly affix the Movement Restriction Cage 10 to a wearer's hand, one simply places the palm of the hand over wrap inside 25, such that the mid-point of the palm is located directly over lower insert elevation 97. At that point, upper insert cover 60 is placed over the back of the wearer's hand, and cage closure loops 80 are pressed onto cage closure hooks 70 to provide a comfortable encirclement of the wearer's wrist.

To apply the movement restriction cage to the other hand, one simply opens one of the insert closures 67 to expose lower insert 55, removes lower insert 55 via lower insert opening 52, turns lower insert 55 over, and replaces lower insert 55 back into its pocket, lower insert 55 now facing "down" instead of "up" (or up, instead of down). Cage closure loops 80, applied to wrap inside 25, are now pressed onto cage closure hooks 70, applied to wrap outside 90, so as to engage each other and provide comfortable encirclement of the wearer's other wrist.

Mouse toy 92 can be applied to the top of the movement restriction cage 10 as a decorative accessory. Also, pad 93 can be inserted between the movement restriction cage 10 and the back of the wearer's hand to further reduce the range of allowed motion (explained in more detail below).

Turning now to FIG. 4, a cross sectional view of lower insert 55 as confined between lower insert cover 50 and wrap 20 can be seen. Here it is clearly shown that lower insert 55 is formed into an upwardly curving member at lower insert bend 95 so as to terminate in lower insert elevation 97. When the wearer has applied the Movement Restriction Cage 10 to his hand, lower insert bend 95 is located at a point approximately ½"–1" forward from the wrist joint onto the palm of the wearer. Lower insert bend 95 is also formed so as to locate lower insert elevation 97 at approximately the mid-palm point of the wearer. Also clearly illustrated in FIG. 4 is one possible implementation of insert closure 67, seen here as insert closure loops 88 which interact with insert closure hooks 85 to maintain the position of lower insert 55 within the pocket formed by lower insert cover 50 and wrap 20. A similar closure is effected to maintain the position of upper insert 65 in the pocket form by upper insert cover 60 and wrap 20.

The positioning of lower insert 55, along with upper insert 65, are crucial to the effectiveness of the instant invention. That is, when lower insert 55 is positioned as described above, and upper insert 65 is located as shown in FIG. 3 (along the back of the hand and up to the knuckles), both inserts 55 and 65 cooperate with the encircling wrap 20 to limit pronation and supination of the wearer's hand to approximately plus or minus 10°. A pad 93 or rubberized "ball" can be inserted between the upper insert 65 and the hand, or between lower insert 55 and the hand, if needed, to properly limit the amount of pronation and supination. Beyond this limited range, pronation and supination of the wearer's hand is not easily accomplished. Lateral motion of the hand, via the wrist joint, is relatively uninhibited. For additional comfort, the user may insert a felt liner (or other soft material) between the hand and wrap inside 25. Such a liner should be washable and easily removable. Also, mouse toy 92 can be attached to movement restriction cage 10 for entertainment of children.

Figure 5:
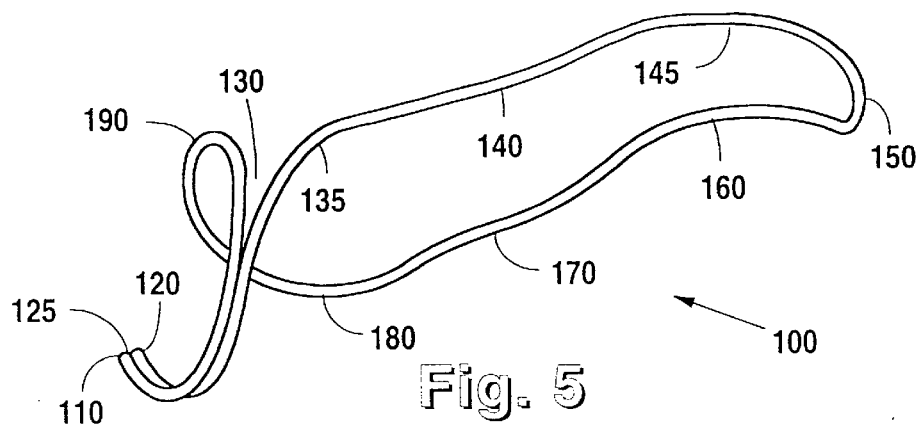
FIG. 5 is a perspective view of the preferred embodiment.
Figure 6:
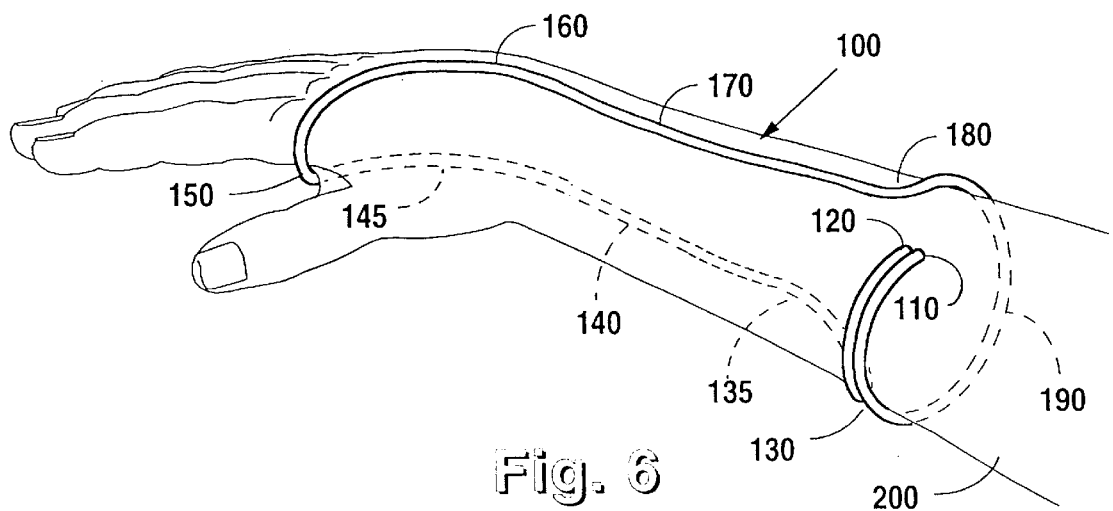
FIG. 6 is a perspective view of the preferred embodiment as applied to a wearer's hand.
Figure 7:
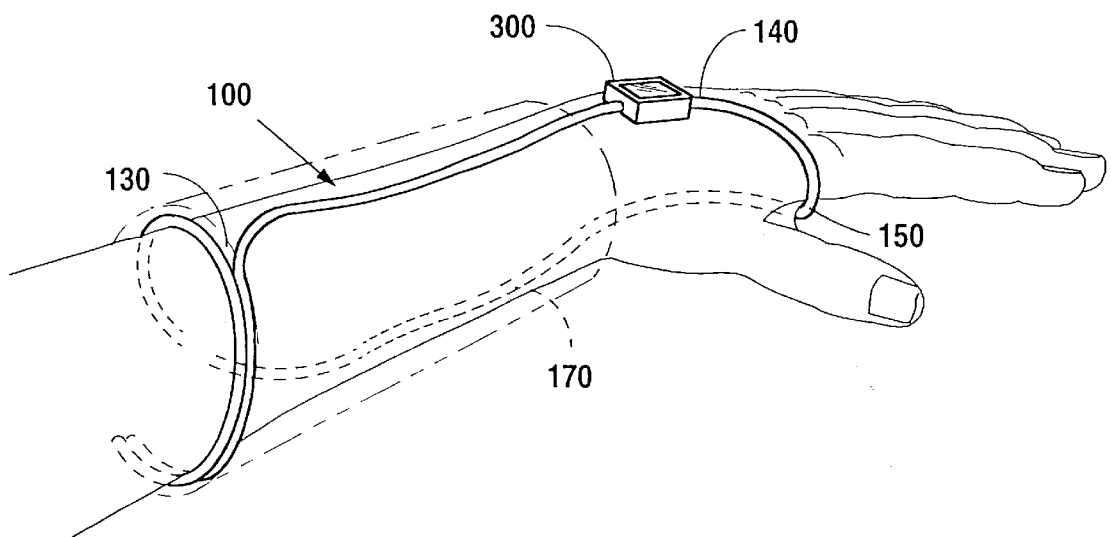
FIG. 7 is a perspective view of the preferred embodiment with attached accessory.

Turning now to FIGS. 5, 6, and 7, the preferred embodiment of the invention can be seen. Here is it clearly shown how the preferred embodiment of the invention can be constructed from a single piece of material. While the alternative embodiment illustrated in FIGS. 1–4 accomplishes most of the advantages inherent in the instant invention, the wrap material tends to prevent free circulation of air with the skin of the wearer, and thus lends itself to bacterial growth and the accumulation of dirt.

The improved Wire Brace (shown in FIG. 5) 100 is to be formed from a single piece of wire or similar material. The actual material used must be able to hold a particular shape, but allow deformation and reformation by the wearer to accommodate various hand sizes and shapes. If the Wire Brace 100 is constructed of metal, near end 110 and far end 120 are joined together at juncture 125 by means of solder, welding, or the like. The juncture is maintained through approximately 90° of a circular bend where at the structure separates into two distinct portions at separation point 130. Whether the Wire Brace is worn on the left or right arm, separation point 130 occurs at some point along the inner side of forearm 200. One element of juncture 125 then goes on to form forearm 200 support bend 135 and continues along the underside of the forearm 200 as lower forearm support 140 (i.e., if the Wire Brace 100 is worn on the right hand, otherwise, lower forearm support 140 travels along the upper side of the forearm 200). Lower forearm support 140 continues to travel in a generally straight line as it crosses the wrist of the wearer and enters the palm region, where it forms palm support bend 145 at a point approximately midway along the palm of the wearer. Palm support bend 145 is a relatively sharp bend and directs the wire structure towards a point located approximately ½" to 1" away from the juncture of the thumb and index finger, where it crosses the inside of the palm at transition bend 150. The structure of the Wire Brace 100 continues across the back of the hand in a direction parallel to the knuckles, where another relatively sharp bend is encountered, backhand support 160. The structure of the Wire Brace 100 is then directed across the remainder of the back of the hand, across the wrist joint, and in a generally straight line along the upper portion of the forearm 200 to constitute upper forearm support 170. At a point approximately 1–½" away from juncture 125, the upper forearm support 170 forms encirclement bend 180 which continues around the side of forearm 200 opposite to that where separation point 130 is located to form mid-arm support 190, and to join separation point 130 thereafter.

Turning now to FIG. 7, the Wire Brace 100 as applied to the left hand can be seen. Also illustrated is accessory 300 which is attached at some point along lower forearm support 140, between separation point 130 and transition bend 150. Accessory 300 may be a watch, a pager, a pen holder, a child's toy, or some other useful accessory desired by the wearer. If worn on the right arm, accessory 300 will be located at a point along upper forearm support 170, between separation point 130 and transition bend 150. Accessory 300 may also constitute items of jewelry, or in the case of children, fanciful animals such as a mouse, cat, or bear, etc. Accessory 300 will normally be located at some point on the back of the wearer's hand.

While the appearance of the preferred embodiment illustrated in FIGS. 5–7 is quite different from that of an alternative embodiment illustrated in FIGS. 1–4, it can now be appreciated that functionally the two are equivalent, with the exception that the preferred embodiment allows increased lateral mobility, while providing a relatively restricted movement range for pronation and supination of the wearer's hand. Also, the preferred embodiment does not closely surround the wearer's arm with fabric, and is thus amenable to recreational activities such as swimming. Finally, the unique construction of the preferred embodiment allows the Wire Brace 100 to emulate jewelry or other decoration so as to provide an improved aesthetic appearance for all wearers.

Figure 8:
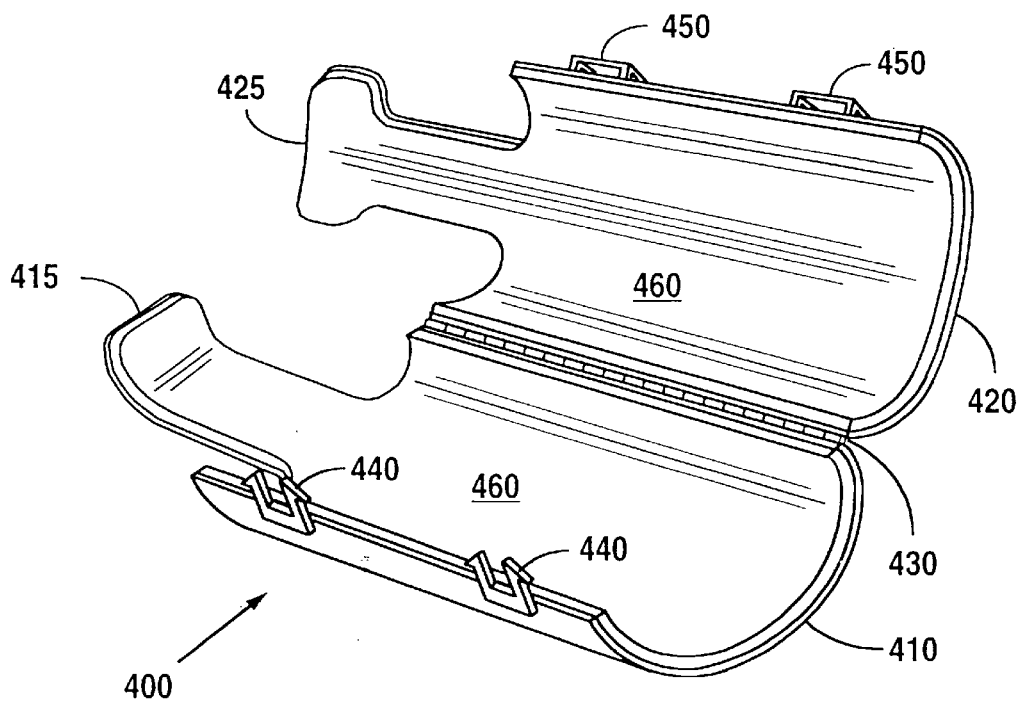
FIG. 8 is a perspective view of a second alternative embodiment.
Figure 9:
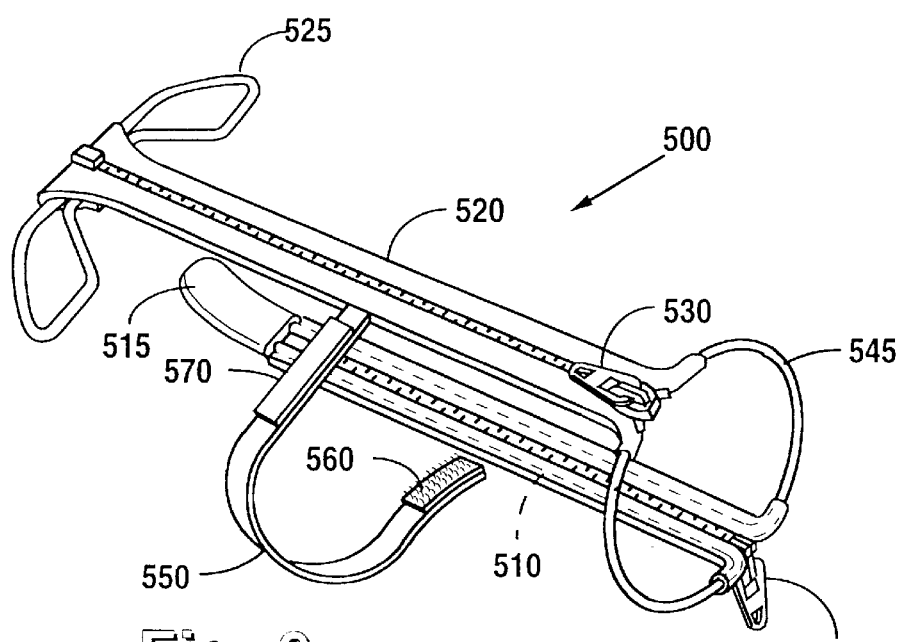
FIG. 9 is a perspective view of a third alternative embodiment.

Turning now to FIGS. 8 and 9, a second and third alternative embodiment of the instant invention can be seen.

In FIG. 8, Turtle Cage (TC™) 400 can be seen to comprise lower frame 410 with palm support 415 connected to upper frame 420, with backhand support 425 by way of hinge 430. To apply the Turtle Cage 400 to the wearer's hand, the hand is placed within the confines of the lower frame 410 and upper frame 420 so that the mid-palm area rests upon palm support 415. Thereafter, lower frame 410 and upper frame 420 are brought together so as to engage catches 440 with closures 450. In use, Turtle Cage 400 functions similarly to the device shown in FIGS. 1–4, but is of a more rigid construction, and therefore, less desirable for the user. It is also less permeable to the environment, which makes it less comfortable to wear. It is assumed that lower frame 410 and upper frame 420 are both constructed of a plastic-like material which is semi-rigid or rigid material. It is likely that a cushioning material, such as foam 460 will be used to increase user comfort in this design. The particular advantage of Turtle Cage 400 is that it is durable enough to be used in rough and tumble play by athletes and children, and also provides a protective enclosure for the traumatized wrist, similar to a cast. Also, a larger, padded version of Turtle Cage 400 can be purchased for children and by changing the amount of foam 460 in the interior, physical growth of the child can be accommodated.

Turning now to FIG. 9, a third alternative embodiment, Glove Cage (GC™) 500 is illustrated. This particular alternative embodiment provides more of the advantages of the preferred embodiment than does either that illustrated in FIG. 8 or in FIGS. 1–4, and is designed to be worn within a glove-like structure (see FIG. 10, illustrating glove cage assembly 600 and glove 610). However, it is much more difficult to manufacture than the preferred embodiment, and not as easily applied to the wearer's arm. As shown in FIG. 9, lower forearm brace 510 is formed from a semi-rigid material, such as wire, to form a track along which lower zipper 535 runs, so as to terminate in palm restraint 515. This element of the alternative embodiment functions in a similar fashion to the lower frame 410 and palm support 415 shown in FIG. 8. To allow entry of the wearer's hand and forearm through forearm cage 545, upper zipper 530 and lower zipper 535 are opened to provide a greatly increased encirclement area. Once the device is positioned appropriately on the wearer's arm, that is, so that palm restraint 515 is located at approximately the mid-palm point, upper and lower zippers 530 and 535 are closed. While this particular construction, which involves forearm cage 545, is somewhat amenable to varying sizes of forearms, it is not nearly so adaptable as the design provided by the preferred embodiment. Upper zipper 530 runs along a track formed by upper forearm brace 520 and terminates in backhand restraint 525. Upper forearm brace 520 and backhand restraint 525 also function similarly to the upper frame 420 arid backhand support 425 of FIG. 8.

This glove cage 500 can be used without a glove (as shown in FIG. 9), but instead of catches and closures, this particular embodiment illustrates the use of a strap 550 to encircle the wearer's forearm, which is secured by the interaction of strap hooks 560 with strap loops 570.

While the invention has been described with specific reference to wire as the preferred material for construction of the Wire Brace, other materials can be used. The most desirable would be some type of semi-rigid plastic which was light in weight, inexpensive, and that could be formed to permanently retain various shapes. The most desirable material would also be non-abrasive to the human skin, but in lieu thereof, a rubberized or foam coating could be applied to wire or other material that is used to construct the Wire Brace.

Likewise, while the preferred embodiment, along with three alternative embodiments has been discussed herein, it is contemplated that other alternative embodiments which make use of an easily applied wrist restraint which acts to allow a limited range of pronation and supination of the wearer's hand, within a range of approximately plus or minus 10° (or less), and easily applied to either hand, can be effected within the spirit of this invention.

Although the invention has been described with reference to specific embodiments, this description is not meant to be construed in a limited sense. Various modifications of the disclosed embodiments, as well as alternative embodiments of the invention, will become apparent to persons skilled in the art upon reference to the detailed description and summary of the invention above. It is, therefore, contemplated that the appended claims will cover such modifications that follow within the scope of the invention.

I claim:

1. A wrist brace of unitary construction useful for therapeutic recovery and restraint of pronation and supination of a hand of a user wearing said wrist brace while allowing relatively unrestrained lateral movement of the hand with respect to the forearm, comprising:

an upper forearm support;

a lower forearm support connected to said upper forearm support;

a palm support connected to said lower forearm support;

a backhand support, said back hand support connected to said upper forearm support and said palm support at a transition bend, said bend being located at a juncture of a thumb and index finger during the use of said brace; and said wrist brace formed from a single piece of wire capable of holding a particular rigid shape and configured to allow a wrist of the user to be secured within ten degrees of supination or pronation.

2. The wrist brace of claim 1 wherein said single piece of material has a near end and a far end.

3. The wrist brace of claim 2, wherein said near end is securely attached to said far end.

4. The wrist brace of claim 1, wherein said wrist brace is configured to secure a wrist without significant lateral movement restriction.

5. The wrist brace of claim 1, wherein said wrist brace is ambidextrous with respect to its ability to secure a wrist.

6. The wrist brace of claim 1, wherein said single piece of material may be deformed and reformed to accommodate varying hand, wrist and forearm sizes and shapes.

* * * * *